United States Patent [19]

Shesol et al.

[11] Patent Number: 5,843,018

[45] Date of Patent: Dec. 1, 1998

[54] DISPOSABLE STERILE EMOLLIENT CARRIER DEVICE

[75] Inventors: Barry F. Shesol, Aurora; George Glumac, Montrose, both of Colo.

[73] Assignee: Tapeless Technologies, Inc., Denver, Colo.

[21] Appl. No.: 660,548

[22] Filed: Jun. 7, 1996

[51] Int. Cl.⁶ ..................................................... A61F 13/00
[52] U.S. Cl. ................................. 602/79; 602/41; 602/48
[58] Field of Search .................................. 602/41–51, 60, 602/61, 62, 63, 64, 65, 74, 75–79, 13, 48; 604/304, 306, 308; 607/96, 108–112, 114; 128/888, 889, 893, 894, 878, 879, 881, 882; 424/445–449; 2/170

[56] References Cited

U.S. PATENT DOCUMENTS

| | | |
|---|---|---|
| 1,925,615 | 9/1933 | Stuart . |
| 3,245,406 | 4/1966 | Chardack .................................. 602/79 |
| 3,595,235 | 7/1971 | Jespersen .................................. 602/41 |

*Primary Examiner*—Richard J. Apley
*Assistant Examiner*—Kim M. Lee
*Attorney, Agent, or Firm*—Edwin H. Crabtree; Ramon L. Pizarro; Donald W. Margolis

[57] ABSTRACT

A disposable sterile emollient carrier device for delivering an application of an emollient is described. The carrier device is to be used for treatment of simple and/or complex cutaneous injuries and disorders on different parts of the human body. The disposable emollient carrier device includes an elongated bidirectional (stretches longitudinally) wrap having a bonded or movable emollient carrier platform thereon. The carrier platform may be either a medical grade foam sheeting surface or a porous mesh pocket. The foam sheeting surface allows the emollient to be applied directly to it, and then the combination applied to an intended area to be treated. Similarly, the mesh pocket receives the emollient therein and the emollient is dispensed through a porous front surface of the pocket to the wound. Both the foam sheeting surface and the mesh pocket include an impermeable back surface to prevent the emollient from bleeding onto the wrap. The wrap may vary in size and shape to accommodate various anatomic locations. The bidirectional wrap is adaptable for conforming to various parts of the anatomy of a patient and includes a releasable hook fastener at one end for securing the end to any portion of the wrap along its length. The wrap is made of a loose weave stretch bonded laminate material. Also, the wrap may use pressure sensitive tape mounted at the ends of the wrap for securing the carrier device to or around the body.

15 Claims, 2 Drawing Sheets

U.S. Patent Dec. 1, 1998 Sheet 1 of 2 5,843,018
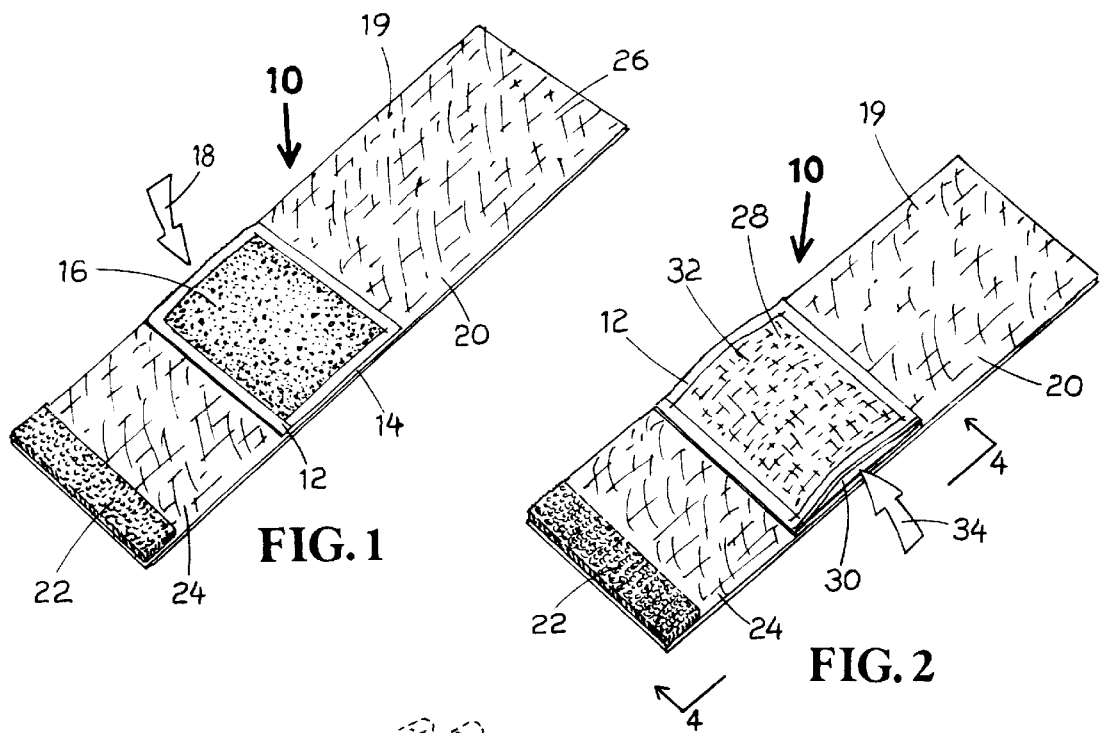
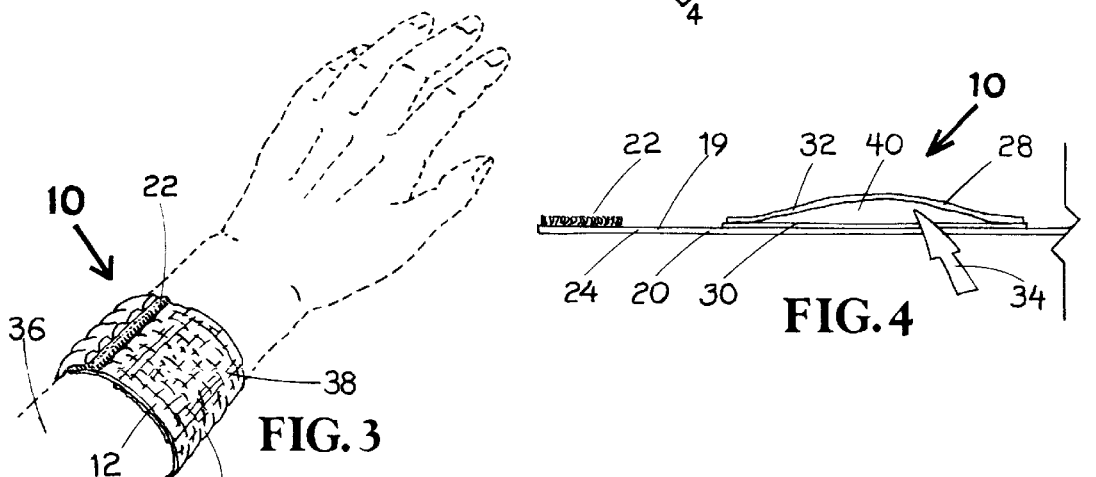
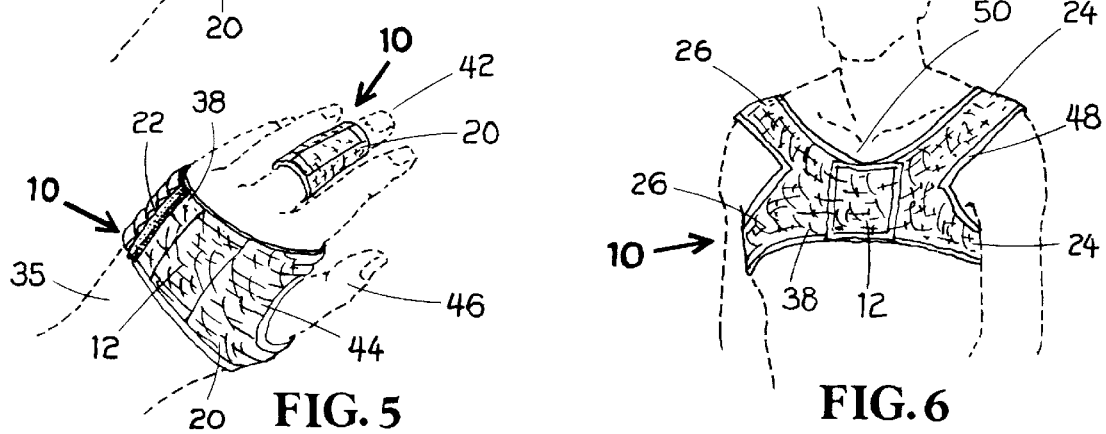

DISPOSABLE STERILE EMOLLIENT CARRIER DEVICE

BACKGROUND OF THE INVENTION (a) Field of the Invention This invention relates to wound dressings and wound bandages and more particularly, but not by way of limitation, to a disposable sterile emollient carrier device having a wrap for holding a bonded or movable emollient carrier platform thereon.

(b) Discussion of Prior Art In the day to day treatment of simple and complex cutaneous injuries and disorders, the topical application of an emollient is often the treatment of choice, The traditional method of application entails manually applying a compound to the injury site with one's fingers or an applicator and then often requires a secondary dressing of gauze or a similar material to do the following:

a. Keep the compound from wiping away from its intended location.
b. Protect other sites or articles such as clothing from contamination.
c. Provide additional protection to underlying tissues.
d. Keep the site or emollient from desiccating (drying out), thereby losing the potency and effectiveness of the emollient.
e. Assist the absorption of the emollient into the treated tissues.

Frequent problems encountered by this traditional means of manual application include:

1. Loss of sterility because of application technique unless preserved by the use of sterile gloves at an added expense.
2. Harm to the injury site caused by rubbing of fingers or applicator over the treated area.
3. Inconsistent thickness of emollient caused by the manual application. Some products work best as a thin layer while others work best as a thick area.
4. Requires a "clean up" process after the application process.
5. May require the assistance of a second person to apply the compound if the patient is unable to reach or see the area to be treated.

If a product existed that would include as a unit a carrier for an emollient and a protective covering for the tissue which could be applied "en bloc" by the patient and in a sterile setting, then the above outlined problems, additional material expenses and inconveniences would be avoided. This invention addresses these problems for the benefit of the patient and improved health care.

Heretofore there have been a variety of different types of wound dressings using adhesives and stretchable wraps such as described in the following patents.

U.S. Pat. No. 4,732,146 to Fasline et al. discloses a surgical wound dressing device having a frame with an opening for receiving different types of wound dressings. A dressing is held in place by straps attached to one side of the frame with one end of the straps including releasable Velero fasteners.

U.S. Pat. No. 4,917,112 to Kalt describes a bandage having an opening with the opening covered with a transparent membrane. The membrane is designed to allow air and vapors to permeate outward from the wound and prevent contaminants from entering in the opposite direction.

In U.S. Pat. No. 4,909,243 to Frank et al., a two piece wound dressing is shown having an adhesive layer on one side of a baseplate with an opening in the baseplate to expose the wound and the epithelium area around the wound. A second adhesive layer on one side of a wound pad secures a wound dressing above the opening in the baseplate.

U.S. Pat. No. 4,907,579 to Kum, U.S. Pat. No. 5,167,613 to Karami et al., and U.S. Pat. No. 3,779,242 to McCullough disclosed different types of adhesive bandages for providing open areas to wounds to enhance healing. In U.S. Pat. No. 5,036,838 to Sherman, a foam plastic orthopedic fabric is described having a Velcro tab at one end of the fabric.

In U.S. Pat. No. 4,470,410 to Elliott a stretchable sleeve is shown with Velcro fasteners at the ends of the sleeve. The sleeve includes a central opening with a releasable flap for retaining an intravenous tube or the like.

U.S. Pat. Nos. 4,709,695 to Kohn et al., 4,399,816 to Spangler, 5,086,763 to Hathman, and 4,926,883 to Strock all describe different types of wound surrounding dressings and bandages. Also U.S. Pat. Nos. 4,190,054 to Brennan and 4,658,811 to Beaird disclose stretchable bandages having loop and hook type attachment ends for encircling the head of a patient.

In U.S. Pat. No. 5,456,660 to one of the subject inventors, a wound dressing support device is described for holding a variety of standard gauze pads in place on top of an open wound. The device includes an elongated unidirectional wrap with a window opening therethrough. Around the sides of the window is a non-adhesive fastener for releasably engaging a portion of the sides of the gauze pad.

None of these prior art patents disclose the unique structure and advantages of the subject invention as described herein when addressing the need of a disposable sterile emollient carrier for delivering an application of an emollient to an area to be treated.

SUMMARY OF THE INVENTION

In view of the foregoing, it is an object of the present invention to provide a disposable sterile emollient carrier device which will deliver an application of an emollient directly to an area to be treated. The device includes a wrap using e bidirectional material which prevents slippage either up or down on the area being treated.

Another object of the invention is to provide an emollient carrier with a wrap that eliminates the need of adhesive tape which causes pain during removal, possible allergic reactions, and flimsy application due to hair, moisture and wound complications. Adhesives also do not allow for readjustment of tension for unlimited times.

Still another object of the subject emollient carrier is the use of a carrier platform in the form of a foam sheeting surface or mesh pocket which carries the emollient thereon and applies the emollient directly to the area to be treated.

Yet another object of the emollient carrier device is that the bidirectional wrap may be provided with hook fasteners at one end for engaging a portion of loop like material of the wrap allowing for easy adjustment in either loosening or tightening the wrap when the carrier platform is received over the wound. The carrier device is designed so that there is no excess material or use of supplies, thus keeping down the cost of health care. Also, decreased bulk of materials means less biohazardous wound materials and consequently less cost of removal of these materials.

A further object of the invention is that the carrier device is lightweight, nonconstricting, versatile and able to be applied by a single individual. Further, the wrap is bidirectional and therefore stretchable longitudinally along its length for versatility in conforming to different parts of the anatomy of the trunk, the hand, the head and the limbs. This feature also limits slippage, avoiding the need for ancillary dressing support techniques, In summation, the subject invention eliminates the deficiencies of other prior art emollient carrier systems while offering the following objects and advantages that support, simplify, and promote wound healing. They are:

a. a disposable, sterile, lightweight and non-allergenic wound care device.

b. ease in application and removal by the patient and at a distance from the wound, not requiring, in most instances, the use of more than one hand. This feature has benefits to both the patient and the health care provider. It keeps the application and removal at a distance from the wound benefitting the aspects of comfort, less trauma to the wound site and avoidance of secondary contamination.

c. adaptable to different anatomic locations and wound sizes.

d. preserves the integrity of the skin by avoiding adhesives and abrasive materials.

e. allows frequent dressing changes with minimal disruption to the wound bed or local tissues.

f. improves patient compliance by nature of its simplicity and ease.

g. reduces chances of contamination and exposure to health care providers.

h. reduces biohazardous materials and cost of their removal.

The subject disposable emollient carrier device includes an elongated bidirectional (stretches longitudinally) wrap having a bonded or movable emollient carrier platform thereon. The carrier platform may be either a medical grade foam sheeting surface or a porous mesh pocket. The foam sheeting surface allows the emollient to be applied directly to it, and then the combination applied to an intended area to be treated. Similarly, the mesh pocket receives the emollient therein and the emollient is dispensed through a porous front surface of the pocket to the wound. Both the foam sheeting surface and the mesh pocket include an impermeable back surface to prevent the emollient from bleeding onto the wrap. The wrap may vary in size and shape to accommodate various anatomic locations. The bidirectional wrap is adaptable for conforming to various parts of the anatomy of a patient and includes a releasable hook fastener at one end for securing the end to any portion of the wrap along its length. The wrap is made of a loose weave stretch bonded laminate material. Also, the wrap may use pressure sensitive tape mounted at the ends of the wrap for securing the carrier device to or around the body. Further, one end or both ends of the wrap may be bifurcated for receipt-around various parts of the human anatomy or the wrap may include a hole in a portion of the wrap for receiving a body member therethrough.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a perspective view of the emollient carrier device having a carrier platform with a medical grade foam sheet surface. The foam sheet surface receives an application of emollient thereon for application directly to an area to be treated. The carrier platform is fused on top of a portion of an elongated bidirectional wrap having a releasable hook fastener at one end of the wrap.

FIG. 2 is a perspective view of another embodiment of the emollient carrier device having a carrier platform with a mesh pocket, The emollient is received inside the pocket and the medication bleeds through a porous front surface onto an area to be treated. The carrier platform is fused oh top of a portion of an elongated bidirectional wrap having a releasable hook fastener at one end of the wrap.

FIG. 3 is a perspective view of a human hand and arm with the emollient carrier device received around a portion of the arm.

FIG. 4 is a side sectional view of a portion of the emollient carrier device taken along lines 4—4 shown in FIG. 2.

FIG. 5 is a perspective view of a human hand with a smaller emollient carrier device received around a finger and another emollient carrier device received on top of the hand with the wrap having a hole therein for receiving a thumb therethrough, FIG. 6 is a perspective view of a portion of the upper human body with the emollient carrier device with opposite ends of the wrap bifurcated for receipt over the shoulders and below the arms of the body with the wrap secured at the back of the body. The emollient carrier platform received over a portion of the chest to be treated.

DESCRIPTION OF THE PREFERRED EMBODIMENTS

Figure 7:
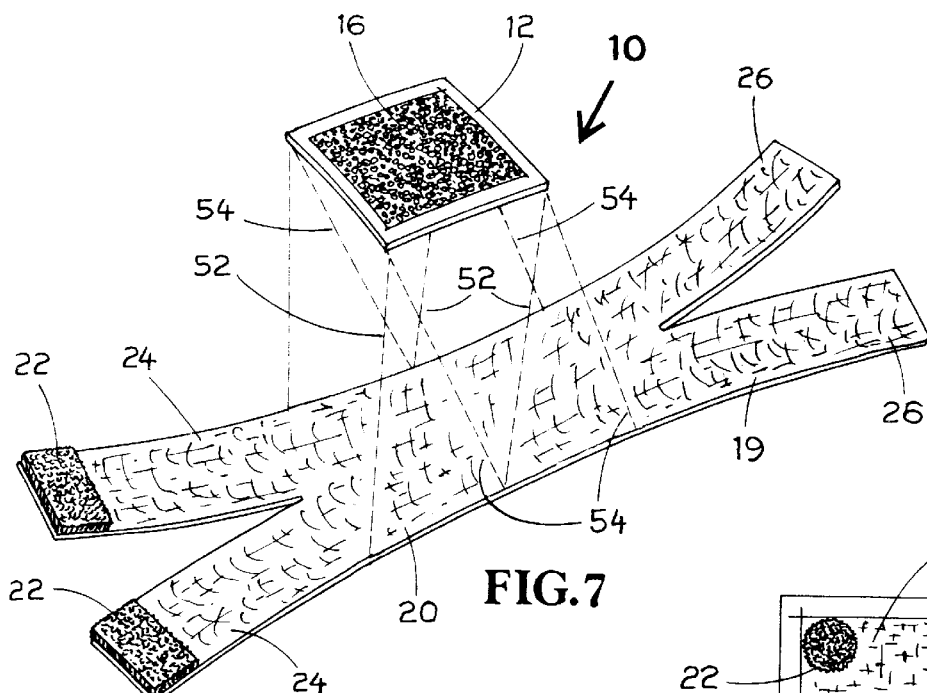
FIG. 7 is a perspective view of the emollient carrier device with the carrier platform movable on the wrap for adjustment of the carrier platform over a wound site.

In FIG. 1, a perspective view of the emollient carrier device is shown having a general reference numeral 10. The carrier device 10 includes a carrier platform 12 with an impermeable back surface 14 and a medical grade front foam sheet surface 16 mounted on top of the back surface 14. The front foam sheet surface 16 is designed to receive an application of emollient as indicated by arrow 18 thereon for applying directly to an area to be treated.

The carrier platform 12 is bonded on top of a portion of a front side 19 of an elongated bidirectional wrap 20 having releasable hook fasteners 22 at one end 24 of the wrap 20. While the hook fasteners 22 are shown, it can be appreciated that the end 24 and an opposite end 26 of the wrap could have different types of fasteners such as pressure sensitive tape, adhesives and the like. The wrap 20 is bidirectional along it's length for stretching the wrap 20 when it is applied around a portion of the body or limb. The width of the wrap 20 is not expandable or stretchable for preventing the distortion and slippage of the carrier platform 12 when in use. The wrap's length may vary from 6 inches to 4 feet and greater. The wrap's width may vary from 1 inch to 12 inches and greater. The wrap 20, for example, is made of a stretch bonded laminate. The wrap 20 includes a loose loop-like weave on the front and back surfaces of the wrap for engaging the hook fasteners 22. An important feature of the invention is the use of the hook fasteners 22 to engage the loose loop-like weave of the wrap 20 along any portion of it's length. This feature makes the carrier device 10 infinitely adjustable along the length of the wrap 20 for ease in tightening or loosening the device 10.

FIG. 2 is a perspective view of another embodiment of the emollient carrier device 10 with the carrier platform 12 having a mesh pocket 28. The mesh pocket 28 includes an impermeable back surface 30 and a permeable or porous front surface 32. The application of emollient is received inside the pocket 28 as indicated by arrow 34. The emollient medication then permeates through the porous front surface 32 onto an area to be treated.

FIG. 3 is a perspective view of a human hand 35 and arm 36 with the emollient carrier device 10 received around a portion of the arm 36. As mentioned above, the wrap 20 can be easily adjusted on the various parts of the body and in this example if the wrap 20 on the arm 36 is too tight, the releasable hook fasteners 22 can be quickly released from the loose weave of the wrap 20 and adjusted along the length of the wrap 20. In this view, a back side 38 of the wrap 20 is shown with the carrier platform 12 received over an area being treated on the arm 36.

FIG. 4 is a side sectional view of a portion of the carrier device 10 taken along lines 4—4 shown in FIG. 2. The mesh pocket 28 can be seen with an opening 40 for receiving the emollient therein as indicated by arrow 34. In this view the impermeable back surface 30 of the pocket 28 can be seen on top of the front side 19 of the wrap 20. The impermeable back surface 30 prevents the emollient from contacting and bleeding onto the wrap 20.

FIG. 5 is a perspective view of the human hand 35 with a smaller emollient carrier device 10 received around a finger 42. Also another emollient carrier device 10 is received on top of the hand 35. In this example, the wrap 20 has a hole 44 therein for receiving a thumb 46 therethrough. It can be appreciated that the wrap 20 can easily be adapted with holes 44 for conforming to various parts of the anatomy of the patient.

FIG. 6 is a perspective view of a portion of the upper human body 48. In this example, the emollient carrier device 10 has the wrap 20 with opposite ends 24 and 26 bifurcated for receipt over the shoulders and below the arms of the body 48 with the wrap 20 secured at the back of the body. The bifurcated ends 24 can include the hook fasteners 22 for attachment to a portion of the bifurcated ends 26. This attachment is not shown in the drawings but would be similar to the securing of the carrier device as shown in FIGS. 3 and 5. The emollient carrier platform 12 is received over a portion of a chest 50 to be treated. The use of the bifurcated ends 24 and 26 in this drawing is but one example of the flexibility of the carrier device 10 for being contoured for the treatment of simple and complex cutaneous injuries and disorders on various parts of the human anatomy.

FIG. 7 is a perspective view of the emollient carrier device 10 similar to the carrier device shown in FIG. 6. In this view, the front side 19 of the wrap 20 is shown with the ends 24 and 26 bifurcated for ease in particular applications on the human body. The carrier platform 12 is shown as being releasable and movable along the length of the wrap 20. Dotted lines 52 illustrate one location the carrier platform 12 can be secured on the wrap 20 while dotted lines 54 show another location on the wrap 20 for placing the carrier platform 12 thereon. Obviously, the ability to move the carrier platform 12 to different positions on the wrap 20 provides greater flexibility in placing the emollient directly over the wound to be treated. This is particularly true where a wound may be difficult to reach and treat on the body. The carrier platform 12 may have a front foam sheet surface 16 as shown in this drawing or the carrier platform 12 may have a mesh pocket 28 with a porous front surface 32 and impermeable back surface 30.

Figure 8:
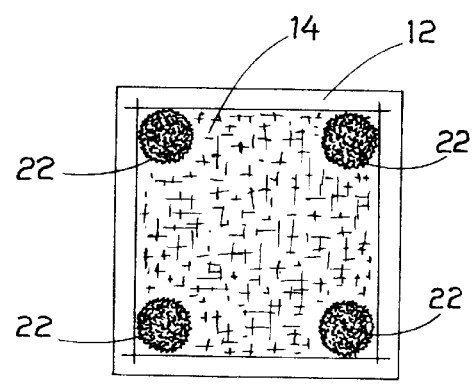
FIG. 8 is a rear view of the carrier platform shown in FIG. 7 and having hook fastener tabs for releasable engagement from the surface of the wrap.

FIG. 8 is a rear view of the carrier platform 12 shown in FIG. 7 and having hook fastener 22 in the form of tabs attached to the impermeable back surface 14. The hook fasteners 22 are used for releasable engagement from the loose loop-like weave surface of the wrap 20. In this manner the carrier platform 12 is movable and can be placed at various position along the length of the wrap 20.

While the invention has been particularly shown, described and illustrated in detail with reference to the preferred embodiments and modifications thereof, it should be understood by those skilled in the art that changes in form and detail may be made therein without departing from spirit and scope of the invention as claimed, except as precluded by the prior art.

The embodiments of the invention for which an exclusive privilege and property right is claimed are defined as follows:

1. A disposable sterile emollient carrier device for delivering an application of an emollient, the carrier device used for treatment of simple and complex cutaneous injuries and disorders on different parts of the human body, the carrier device comprising:

an emollient carrier platform adapted for receiving emollient thereon, said emollient carrier platform being a primary wound dressing;

an elongated non-adhesive wrap having a top and a bottom, said carrier platform attached to a portion of the top of said wrap; and securing means attached to a first end portion of said wrap for releasably engaging a portion of said non-adhesive wrap at any desired location along it's length and securing said wrap on the human body.

2. The carrier device as described in claim 1 wherein said carrier platform is a medical grade foam sheeting surface.

3. The carrier device as described in claim 2 wherein said carrier platform includes a impermeable back surface disposed next to the foam sheeting surface.

4. The carrier device as described in claim 1 wherein said carrier platform is releasably attached to said wrap for repositioning along a length of said wrap.

5. The carrier device as described in claim 1 wherein said carrier platform is a porous mesh pocket.

6. The carrier device as described in claim 5 wherein said mesh pocket includes an impermeable back surface disposed next to a porous front surface, said mesh pocket having an opening therein for receiving an application of emollient therein.

7. A disposable sterile emollient carrier device for delivering an application of an emollient, the carrier device used for treatment of simple and complex cutaneous injuries and disorders on different parts of the human body, the carrier device comprising:

an emollient carrier platform adapted for receiving the emollient thereon, said platform having an impermeable back surface and a porous front surface, said emollient carrier platform being a primary wound dressing;

an elongated bidirectional non-adhesive wrap expandable along the length of said wrap, said wrap having a top and a bottom, the impermeable back surface of said carrier platform attached to a portion of the top of said non-adhesive wrap; and securing means attached to a first end portion of said non-adhesive wrap for engaging a portion of said wrap at any desired location along it's length and securing said wrap on the human body.

8. The carrier device as described in claim 7 wherein the front surface of said carrier platform is a foam sheeting surface for receiving emollient thereon.

9. The carrier device as described in claim 7 wherein said carrier platform is in the form of a pocket with an opening between the porous front surface and the impermeable back surface.

10. The carrier device as described in claim 7 wherein said wrap includes a releasable hook fastener at one end for securing the end to any portion of said wrap along its length, said wrap made of a loose weave material.

11. The carrier device as described in claim 7 wherein said wrap has one end which is bifurcated for ease in receipt around various parts of the human anatomy.

12. The carrier device as described in claim 7, wherein said wrap has opposite ends bifurcated for ease in receipt around various parts of the human anatomy.

13. The carrier device as described in claim 7 wherein the impermeable back surface of said carrier platform includes hook fasteners for releasably attachment to said wrap and for repositioning the location of the carrier platform along a length of said wrap.

14. A method of using a disposable sterile emollient carrier device for delivering an application of an emollient, the carrier device used for treatment of simple and complex cutaneous injuries, wounds and disorders on different parts of the human body, the steps comprising:

adjusting an emollient carrier platform along a length of an elongated non-adhesive wrap and releasably securing said carrier platform thereto;

placing an emollient on said emollient carrier platform, said platform having an impermeable back surface and a porous front surface;

placing said emollient carrier platform over the wound to be treated;

wrapping a first end portion and a second end portion of said non-adhesive wrap around part of the anatomy of the human body; and securing an end of said first end portion along a length of said second end portion of said non-adhesive wrap.

15. The method as described in claim 14 wherein the emollient is placed on a foam sheeting surface of said carrier platform.

* * * * *